(12) United States Patent
Sakimoto et al.

(10) Patent No.: US 9,147,269 B2
(45) Date of Patent: Sep. 29, 2015

(54) RADIATION TOMOGRAPHIC IMAGE GENERATING METHOD, AND RADIATION TOMOGRAPHIC IMAGE GENERATING PROGRAM

(75) Inventors: Tomonori Sakimoto, Kyoto (JP); Kazuyoshi Nishino, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 27 days.

(21) Appl. No.: 14/116,272

(22) PCT Filed: May 30, 2012

(86) PCT No.: PCT/JP2012/003525
§ 371 (c)(1),
(2), (4) Date: Feb. 10, 2014

(87) PCT Pub. No.: WO2012/164921
PCT Pub. Date: Dec. 6, 2012

(65) Prior Publication Data
US 2014/0169650 A1 Jun. 19, 2014

(30) Foreign Application Priority Data

May 31, 2011 (JP) ................. 2011-122080

(51) Int. Cl.
*G06K 9/00* (2006.01)
*G06T 11/00* (2006.01)
(Continued)

(52) U.S. Cl.
CPC ............. *G06T 11/008* (2013.01); *A61B 6/03* (2013.01); *A61B 6/5252* (2013.01); *A61B 6/5258* (2013.01); *G06T 7/0012* (2013.01); *A61B 6/025* (2013.01); *A61B 6/5205* (2013.01); *A61B 6/5235* (2013.01)

(58) Field of Classification Search
None
See application file for complete search history.

(56) References Cited

U.S. PATENT DOCUMENTS 6,721,387 B1 * 4/2004 Naidu et al. ............... 378/8
8,233,586 B1 * 7/2012 Boas ......................... 378/4
(Continued)

FOREIGN PATENT DOCUMENTS

JP  08-019533 A  1/1996
JP  10-337287 A  12/1998
(Continued)

OTHER PUBLICATIONS

International Search Report and the Written Opinion of the International Searching Authority issued in International Application No. PCT/JP2012/003532 dated Jun. 26, 2012, w/ English translation thereof.
(Continued)

*Primary Examiner* — Li Liu
(74) *Attorney, Agent, or Firm* — McDermott Will & Emery LLP

(57) ABSTRACT

An area of an extraneous substance (e.g. area of metal or the like) in images (pre-interpolation projection data in the embodiment) of the extraneous substance (e.g. high-density substance such as metal) extracted and separated by extraction separation in step S1 is interpolated by area interpolation in step S2. Therefore, artifacts can be reduced, while maintaining high spatial resolution, if tomographic images (first tomographic images in the embodiment) are generated by first tomographic image generation in step S3 from the interpolation images interpolated and generated (post-interpolating projection data in the embodiment).

9 Claims, 7 Drawing Sheets

(51) Int. Cl.
*A61B 6/03* (2006.01)
*A61B 6/00* (2006.01)
*G06T 7/00* (2006.01)
*A61B 6/02* (2006.01)

(56) References Cited

U.S. PATENT DOCUMENTS

| | | | |
|---|---|---|---|
| 8,503,750 B2* | 8/2013 | Benson et al. | 382/131 |
| 2004/0264626 A1 | 12/2004 | Besson | |
| 2006/0285737 A1 | 12/2006 | Hamill et al. | |
| 2009/0074278 A1* | 3/2009 | Beaulieu et al. | 382/131 |
| 2010/0183214 A1* | 7/2010 | McCollough et al. | 382/131 |
| 2010/0189331 A1 | 7/2010 | Forthmann et al. | |
| 2011/0007956 A1* | 1/2011 | Meyer et al. | 382/131 |
| 2011/0075911 A1* | 3/2011 | Xing et al. | 382/131 |
| 2011/0135182 A1 | 6/2011 | Goto et al. | |
| 2011/0206258 A1* | 8/2011 | Chen et al. | 382/131 |
| 2012/0237115 A1* | 9/2012 | Rohkohl et al. | 382/154 |

FOREIGN PATENT DOCUMENTS

| | | |
|---|---|---|
| JP | 2010-099114 A | 5/2010 |
| JP | 2010-529876 A | 9/2010 |
| WO | 2010/016425 A1 | 2/2010 |

OTHER PUBLICATIONS

T. Shiomi, "The principle and clinical application of Tomosynthesis—New Technology Produced by FPD," Japan Society of Medical Imaging and Information Sciences magazine, vol. 24, No. 2, 22-27, 2007.

Supplementary European Search Report EP Application No. 12793501.3-1660 dated Oct. 9, 2014.

Yinsheng Li et al., "Metal Artifact Reduction in CT Based on Adaptive Steering Filter and Nonlocal Sinogram Inpainting", Biomedical Engineering and Informatics (BMEI), 2010 3rd International Conference on Biomedical Engineering and Informantics, Oct. 15, 2010, pp. 380-383.

Matthieu Bal et al., "Metal artifact reduction in CT using tissue-class modeling and adaptive prefiltering", Med. Phys. 33 (8), Aug. 2006, pp. 2852-2859.

Koji Kobayashi et al., "A Practical Method to Reducing Metal Artifact for Dental CT Scanners", 19th International Conference on Pattern Recognition, Dec. 8, 2008, pp. 1-4.

Office Action and Search Report Chinese Patent Application No. 201280026498.8 dated Feb. 28, 2015.

Chen Yu, "Study on correction algorithm of metal artifacts in CT images", Wanfang Thesis Database, pp. 27-39, Sep. 28, 2009 with partial English translation and English abstract.

* cited by examiner

RADIATION TOMOGRAPHIC IMAGE GENERATING METHOD, AND RADIATION TOMOGRAPHIC IMAGE GENERATING PROGRAM

CROSS REFERENCE TO RELATED APPLICATIONS

This application is a U.S. National Stage application under 35 U.S.C. §371, of International Application PCT/JP2012/003525 filed on May 30, 2012, which was published as WO 2012/164921 on Dec. 6, 2012, which in turn claims the benefit of Japanese Application No. 2011-122080, filed May 31, 2011. The applications are incorporated herein by reference.

TECHNICAL FIELD

This invention relates to a radiation tomographic image generating method and a radiation tomographic image generating program for generating tomographic images based on a plurality of radiological images acquired by radiation beams respectively emitted from different directions to an inspection object, and more particularly to a technique for generating tomographic images of an inspection object including a portion extraneous (e.g. a high-density substance or low-density substance compared with the substance forming the living body) to a substance forming an area of interest in the inspection object.

BACKGROUND ART

As a conventional radiation tomographic image generating apparatus, there is an X-ray tomographic apparatus, for example. This X-ray tomographic apparatus, as shown in FIG. 7, has an X-ray tube 101 and an X-ray detector 102 which are arranged opposite each other across an inspection object M, and are interlocked such that, synchronously with parallel translation of the X-ray tube 101 along the direction of body axis z which is the longitudinal direction of the inspection object M, the X-ray detector 102 moves parallel in a direction opposite to the parallel translation of the X-ray tube 101. Radiography is conducted continuously, while changing the X-ray emission angle of the X-ray tube 101 to the inspection object M, so that an arbitrary point on a particular sectional plane (reference plane) of the inspection object M will always be in the same position on the X-ray detector 102. With the X-ray tomographic apparatus, apart from such parallel translation (linear scan), various scanning tracks are realized, such as arcuate movement (circular scan) accompanying rotation (about an axis in a shorter direction perpendicular to the body axis z and a horizontal plane) of a C-arm (not shown) holding the X-ray tube 101 and X-ray detector 102 as shown in FIG. 8.

The X-ray tomographic apparatus is also called "Tomosynthesis". To generate tomographic images with the tomographic X-ray apparatus, there are a reconstruction technique called "Shift Addition method" which carries out adding operations while shifting, each by a suitable amount, a plurality of projection data (radiological images) acquired by X-ray beams emitted from different directions (projection angles) to an inspection object, and a reconstruction technique called "Filtered Back Projection (FBP) method" (also called "Filter-Corrected Back Projection method") as used in an X-ray CT (Computed Tomography) apparatus for generating tomographic images by revolving an X-ray tube and an X-ray detector about the body axis of an inspection object (see Nonpatent Document 1, for example).

Take a human body as an example of inspection object, there is a substance that forms the living body as the substance forming an area of interest in the inspection object. As substances of high density compared with this substance forming the living body, there are a metallic artificial joint, external fixator, dental stuffing, and so on. These substances of high density are formed of metal or the like, and the substances of high density compared with living body tissue absorb radiation. In addition, where substances of lower density compared with the substance forming the living body are included, the substances of low density compared with living body tissue transmit radiation.

PRIOR ART DOCUMENT

Nonpatent Document

[Nonpatent Document 1]
Takeshi Shiomi, "Principle and Application of Tomosynthesis—New Technology Produced by FPD", Japan Society of Medical Imaging and Information Sciences magazine, Vol. 24 No. 2, 22-27, 2007.

SUMMARY OF INVENTION

Solution to Problem

However, there are the following problems in carrying out tomography of an inspection object having such metal or the like. That is, when the inspection object includes a high-density substance such as metal, a problem arises, depending on reconstruction techniques, that artifacts (virtual images) appear adjacent the metal or the like in the tomographic images generated. Artifacts will be generated adjacent the metal or the like by the Filtered Back Projection (FBP) method noted above, or the Likelihood Expectation Maximization (ML-EM) method, for example. As a reconstruction technique which inhibits artifacts adjacent the metal or the like, the above Shift Addition method can be cited but its spatial resolution is inferior. Although the description has been made taking high-density substances for example, artifacts will occur also in the case of low-density substances.

This invention has been made having regard to the state of the art noted above, and its object is to provide a radiation tomographic image generating method and a radiation tomographic image generating program which can reduce artifacts while maintaining high spatial resolution.

Solution to Problem

To fulfill the above object, this invention provides the following construction.

A radiation tomographic image generating method of this invention is a radiation tomographic image generating method for generating tomographic images based on a plurality of radiological images acquired by radiation beams emitted from different directions to an inspection object, respectively, the method comprising an extraction separation step for extracting and separating, from the acquired radiological images, images of a substance extraneous to a substance forming an area of interest in the inspection object; an area interpolation step for generating interpolation images by interpolating an area of the extraneous substance, from peripheral regions thereof, in the images of the extraneous substance extracted and separated in the extraction separation step; and a first tomographic image generating step for generating tomographic images from the interpolation images generated with the area of the extraneous substance interpolated in the area interpolation step; an extraneous projection data generating step for generating extraneous projection data which is projection data of the extraneous substance, from differences between the acquired radiological images and the interpolation images; a second tomographic image generating step for generating tomographic images from the extraneous projection data generated in the extraneous projection data generating step; and a tomographic image synthesizing step for synthesizing the tomographic images generated in the above first tomographic image generating step and the tomographic images generated in the second tomographic image generating step.

[Functions and effects] According to the radiation tomographic image generating method of this invention, the extraction separation step extracts and separates, from the acquired radiological images, images of a substance extraneous to a substance forming an area of interest in the inspection object, and the area interpolation step generates interpolation images by interpolating an area of the extraneous substance, from peripheral regions thereof, in the images of the extraneous substance extracted and separated in the extraction separation step. Then, the first tomographic image generating step generates tomographic images from the interpolation images generated with the area of the extraneous substance interpolated in the area interpolation step. Since the area of the extraneous substance in the images of the extraneous substance extracted and separated in the extraction separation step is interpolated in the area interpolation step, artifacts due to the extraneous substance (e.g. metal) are suppressed if tomographic images are generated in the first tomographic image generating step from the interpolation images interpolated and generated. This enables observation of the area of interest adjacent the area of the extraneous substance. As a result, the artifacts can be reduced while maintaining high spatial resolution.

Since the radiological images are data including the extraneous portion and the interpolation images are data with the area of the extraneous substance interpolated, the projection data generated from the differences between the radiological images and the interpolation images becomes projection data of only the area of the extraneous substance (that is, extraneous projection data). Therefore, when the tomographic images are generated from the extraneous projection data in the second tomographic image generating step, the generated tomographic images become tomographic images of only the area of the extraneous substance. As a result, when the tomographic image synthesizing step synthesizes both the tomographic images generated by the first/second tomographic image generating steps, boundaries between the area of the extraneous substance and the other area become clear in the area of interest while reducing the artifacts.

When the second tomographic image generating step generates tomographic images from the extraneous projection data by the FBP method, pixel values of the tomographic images may become negative values. So, the second tomographic image generating step generates the tomographic images by replacing, with a set reference value (e.g. pixel value "0" or a positive value), the pixel values of areas lower than the reference value among the pixel values of the tomographic images generated by the FBP method. Then, the tomographic image synthesizing step synthesizes the tomographic images generated in the first tomographic image generating step and the tomographic images replaced with the reference value in the second tomographic image generating step. As a result, even though the second tomographic image generating step generates the tomographic images from the extraneous projection data by the FBP method, natural tomographic images can be generated, with the pixel values of the tomographic images not becoming negative values, and the boundaries between the area of the extraneous substance and the other area becoming clear in the area of interest.

The second tomographic image generating step may generate the tomographic images by an iterative approximation method. In this case, it may be combined with the FBP method in the first tomographic image generating step. That is, the first tomographic image generating step generates the tomographic images by the FBP method, and the tomographic image synthesizing step synthesizes the tomographic images generated by the FBP method in the first tomographic image generating step and the tomographic images generated by the iterative approximation method in the second tomographic image generating step.

Similarly, the first tomographic image generating step may generate the tomographic images by the FBP method, or may generate the tomographic images by the iterative approximation method.

The extraction separation step noted hereinbefore may extract and separate projection data of the images of the extraneous substance from projection data of the acquired radiological images, or may generate tomographic images from the projection data of the acquired radiological images, extract and separate, from the tomographic images, tomographic images of the images of the extraneous substance, and forward project the extracted tomographic images of the images of the extraneous substance to generate projection data, thereby to extract and separate the projection data generated through the forward projection as the projection data of the images of the extraneous substance.

A radiation tomographic image generating program of this invention is a radiation tomographic image generating program for causing a computer to perform radiation tomographic image generation for generating tomographic images based on a plurality of radiological images acquired by radiation beams emitted from different directions to an inspection object, respectively, the radiation tomographic image generating program comprising an extraction separation step for extracting and separating, from the acquired radiological images, images of a substance extraneous to a substance forming an area of interest in the inspection object; an area interpolation step for generating interpolation images by interpolating an area of the extraneous substance, from peripheral regions thereof, in the images of the extraneous substance extracted and separated in the extraction separation step; and a first tomographic image generating step for generating tomographic images from the interpolation images generated with the area of the extraneous substance interpolated in the area interpolation step; an extraneous projection data generating step for generating extraneous projection data which is projection data of the extraneous substance, from differences between the acquired radiological images and the interpolation images; a second tomographic image generating step for generating tomographic images from the extraneous projection data generated in the extraneous projection data generating step; and a tomographic image synthesizing step for synthesizing the tomographic images generated in the above first tomographic image generating step and the tomographic images generated in the second tomographic image generating step; the computer being caused to perform the processes in these steps.

[Functions and effects] According to the radiation tomographic image generating program of this invention, since the area of the extraneous substance in the images of the extraneous substance extracted and separated in the extraction separation step is interpolated in the area interpolation step, artifacts can be reduced while maintaining high spatial resolution, if tomographic images are generated in the first tomographic image generating step from the interpolation images interpolated and generated.

Advantageous Effects of Invention

According to the radiation tomographic image generating method and the radiation tomographic image generating program of this invention, since the area of the extraneous substance in the images of the extraneous substance extracted and separated in the extraction separation step is interpolated in the area interpolation step, artifacts can be reduced while maintaining high spatial resolution, if tomographic images are generated in the first tomographic image generating step from the interpolation images interpolated and generated.

DESCRIPTION OF EMBODIMENTS

Embodiments of this invention will be described hereinafter with reference to the drawings.

Figure 1:
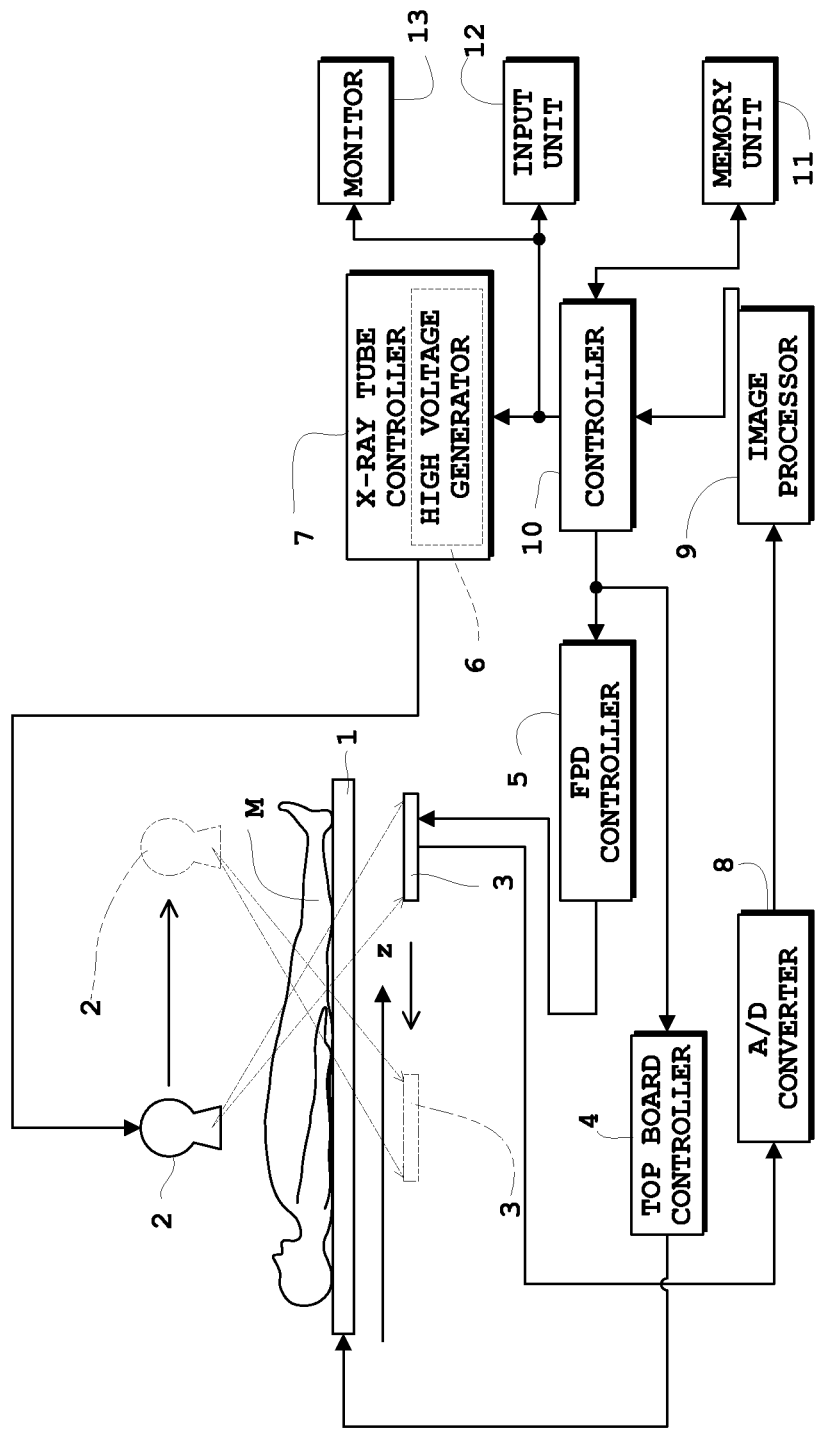
FIG. 1 is a block diagram of a tomographic apparatus according to an embodiment.

FIG. 1 is a block diagram of a tomographic apparatus according to an embodiment. This embodiment will be described taking X-rays as an example of radiation, taking a human body as an example of inspection object, taking a substance forming the living body as an example of substance forming an area of interest in the inspection object, and taking a high-density substance such as a metallic artificial joint, external fixator or dental stuffing as an example of extraneous portion.

The tomographic apparatus, as shown in FIG. 1, includes a top board 1 for supporting an inspection object M, an X-ray tube 2 for emitting X-rays toward the inspection object M, a flat panel X-ray detector (hereinafter abbreviated to "FPD") 3 for detecting X-rays transmitted through the inspection object M.

The tomographic apparatus further includes a top board controller 4 for controlling vertical and horizontal movements of the top board 1, an FPD controller 5 for controlling scanning of the FPD 3, an X-ray tube controller 7 having a high voltage generator 6 for generating a tube voltage and a tube current for the X-ray tube 2, an A/D converter 8 for digitizing and taking out X-ray detection signals which are charge signals from the FPD 3, an image processor 9 for carrying out various processes based on the X-ray detection signals outputted from the A/D converter 8, a controller 10 for controlling each of these components, a memory unit 11 for storing processed images and others, an input unit 12 for the operator to make input settings, and a monitor 13 for displaying the processed images and others.

The top board controller 4 controls the top board 1 to make horizontal movement to move the inspection object M to an imaging position, to make vertical movement, rotation and horizontal movement to set the inspection object M to desired positions, to make horizontal movement during an image pickup operation, and to make horizontal movement for withdrawal from the imaging position after completion of the image pickup. These controls are effected by controlling a top board drive mechanism (not shown) consisting of motors, encoders and so on (not shown).

The FPD controller 5 controls the FPD 3 to make parallel translation along the direction of a body axis z which is a longitudinal direction of the inspection object M. This control is effected by controlling an FPD drive mechanism (not shown) consisting of a rack, a pinion, a motor, an encoder and so on (not shown).

The high voltage generator 6 generates the tube voltage and tube current for emitting X-rays, and applies them to the X-ray tube 2. The X-ray tube controller 7 controls the X-ray tube 2 to make parallel translation in an opposite direction to the parallel translation of the FPD 3. This control is effected by controlling an X-ray tube driver (not shown) consisting of a strut, a threaded rod, a motor, an encoder and so on (not shown).

The X-ray tube controller 7 controls setting of an irradiation field of a collimator (not shown) on the X-ray tube 2. In this embodiment, the irradiation field is set by controlling the collimator to emit X-rays in a fan beam shape spreading in the direction of body axis z.

The image processor 9 and controller 10 are constructed of central processing units (CPUs) and so on. The memory unit 11 is constructed of storage media represented by a ROM (Read-only Memory) and a RAM (Random-Access Memory). The input unit 12 is constructed of pointing devices represented by a mouse, a keyboard, a joy stick, a trackball and a touch panel.

A program and the like for carrying out various image processes are written to and stored in the storage medium represented by a ROM or others. The CPU of the image processor 9 reads from the storage medium and executes the program and the like to carry out image processing corresponding to this program. In particular, by executing the program relating to extraction separation, area interpolation, first/second tomographic image generation, metal or other projection data generation, and tomographic image synthesis, the extraction separation, area interpolation, first/second tomographic image generation, metal or other projection data generation, and tomographic image synthesis corresponding to this program, respectively, are carried out. The program relating to the extraction separation, area interpolation, first/second tomographic image generation, metal or other projection data generation, and tomographic image synthesis corresponds to the radiation tomographic image generating program in this invention.

The memory unit 11 is constructed for storing each image processed by the image processor 9 and written thereto. The FPD controller 5 and X-ray tube controller 7 also are constructed of CPUs and others as are the image processor 9 and controller 10.

Figure 2:
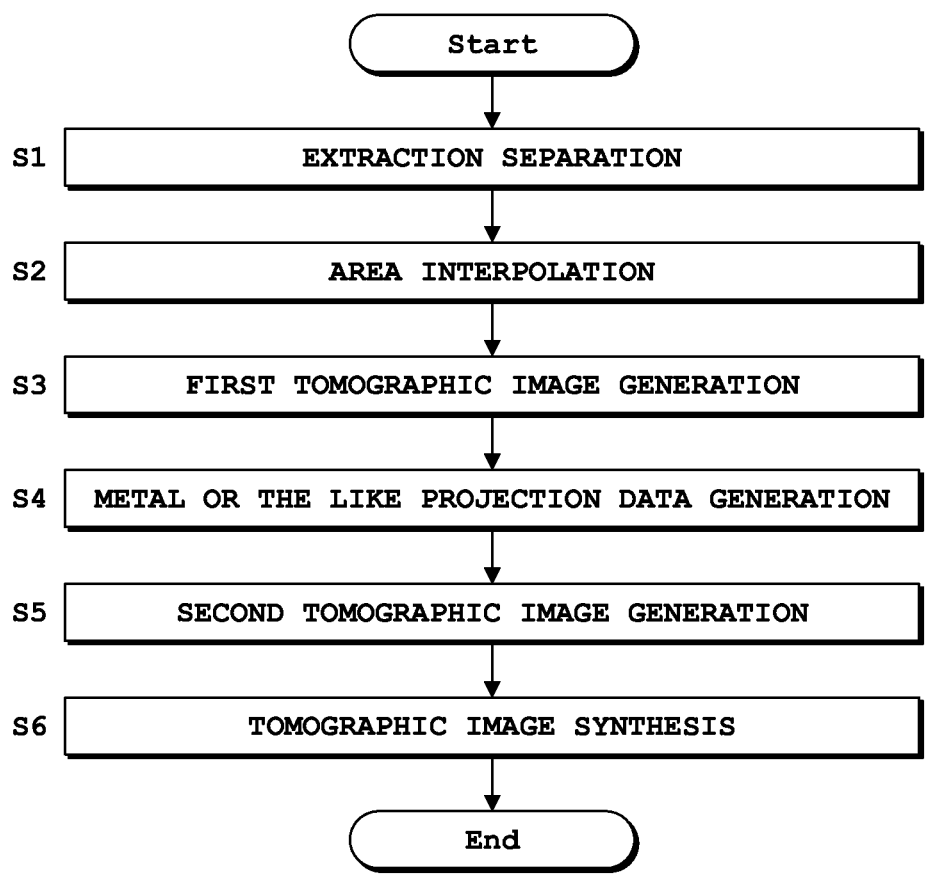
FIG. 2 is a flow chart showing a flow of a series of radiation tomographic image generation by an image processor.
Figure 3:
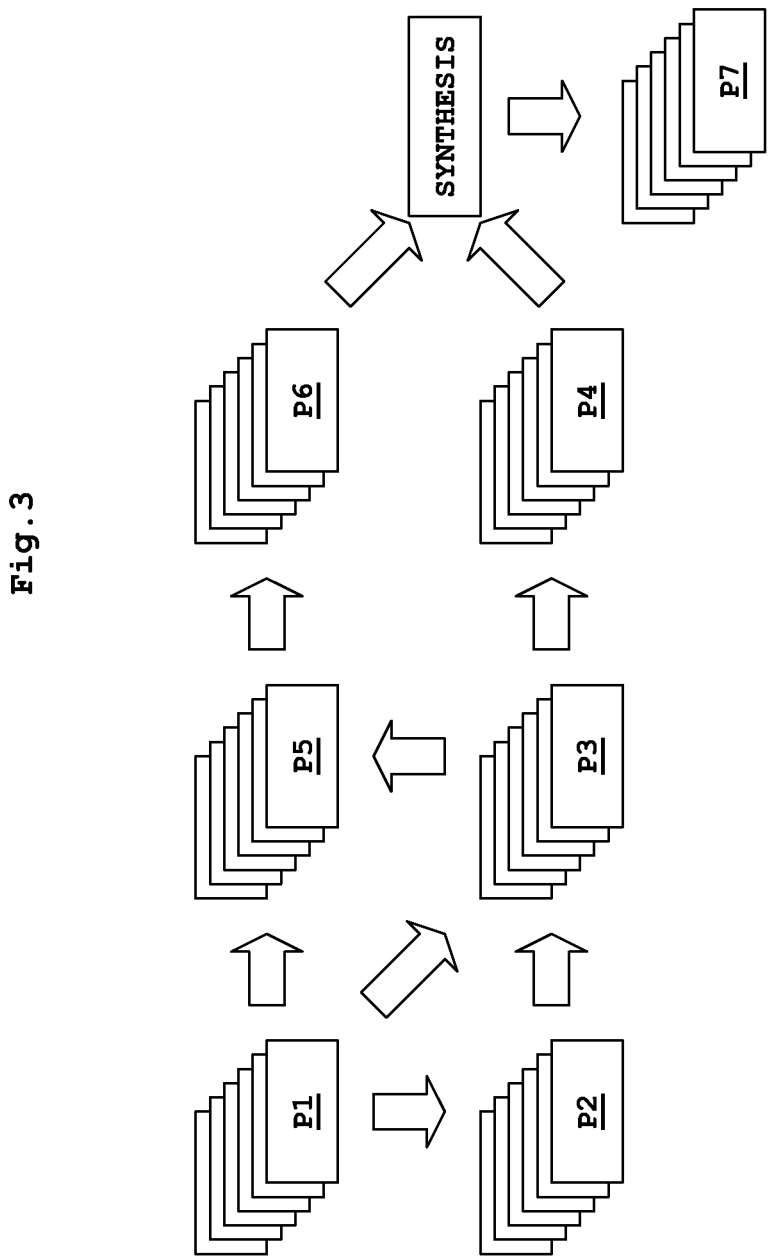
FIG. 3 is a schematic view showing a flow of each image and each data.
Figure 4:
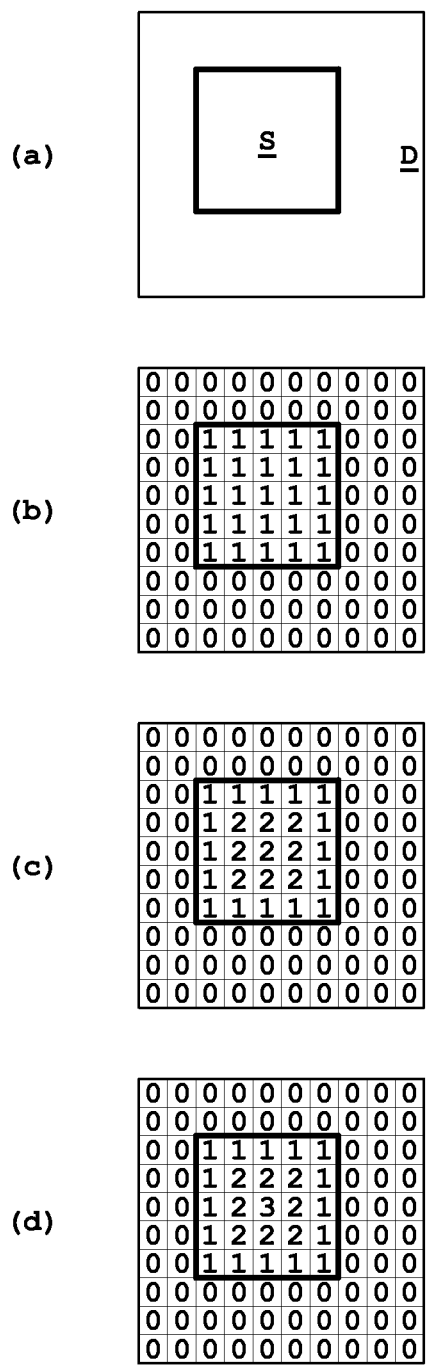
FIGS. 4(a)-(d) are schematic views illustrative of labeling of binarized data.

A flow of radiation tomographic image generation by the image processor 9 will be described with reference to FIGS. 2-4. FIG. 2 is a flow chart showing a flow of a series of radiation tomographic image generation by the image processor. FIG. 3 is a schematic view showing a flow of each image and each data. FIG. 4 is a schematic view illustrative of labeling of binarized data. The radiation tomographic image generation in steps S1-S6 shown in FIG. 2 is carried out by the CPU of the image processor 9 executing the program.

(Step S1) Extraction Separation

As shown in FIG. 1, X-rays in the fan beam shape spreading in the direction of body axis z are emitted from the X-ray tube 2, while causing the X-ray tube 2 and FPD 3 to make parallel translation in opposite directions, as a result of which the FPD 3 detects X-ray beams emitted from different directions (projection angles) to the inspection object M, respectively. Based on the detection by the FPD 3, a plurality of X-ray images are acquired from the X-ray beams emitted from the different directions to the inspection object M, respectively. The X-ray images are projection data projected to the detecting plane of the FPD 3, which are regarded as projection data P1 as shown in FIG. 3.

Images of the high-density substance (metal or the like) are extracted and separated from the acquired projection data P1. As a method of extracting and separating the images of metal or the like, for example, a method is cited which outputs binarized data by carrying out a threshold process on pixel values of the projection data P1, and applying "1" to pixel values higher than a threshold value and "0" to pixel values equal to or below the threshold value (see binarized data D in FIG. 4(a)). In this binarized data, an image area with "1" applied thereto corresponds to an area of the metal or the like extracted and separated, and an image area with "0" applied thereto corresponds to an area of living body tissue (see FIG. 4(b)). This binarized data is regarded as pre-interpolation projection data P2 as shown in FIG. 3. The pre-interpolation projection data P2 corresponds to the images of the extraneous substance in this invention.

(Method A)

The pre-interpolation projection data P2 is extracted and separated from the projection data P1 by carrying out the threshold process on the pixel values of projection data P1 and outputting binarized data in this way. The technique of extraction separation is not limited to the threshold process. There is no limitation to a particular technique, but may be a graph cut technique which carries out extraction separation based on pixel values and pixel value differences, using the presence of edges due to pixel value differences at boundaries between living body tissue and metal, a technique of carrying out extraction separation by frequency band filter using a high spatial frequency at the boundaries between living body tissue and metal, or a usual extraction separation, as exemplified by a level setting method or the like, which extracts and separates images (pre-interpolation projection data P2 in this embodiment) of the substance extraneous to the substance forming the area of interest in the inspection object (the substance forming the living body in this embodiment).

(Method B)

Apart from extracting and separating the pre-interpolation projection data P2 directly from the projection data P1, tomographic images may be generated from the projection data P1 by reconstruction, extracting and separating pre-interpolation tomographic images from the tomographic images by threshold process, for example, and generating projection data by forward projecting the extracted pre-interpolation tomographic images, thereby to extract and separate the forward projected and generated projection data as pre-interpolation projection data P2.

It is also possible to combine the above method A and method B. For example, a case is conceivable where a thick metal is extracted by method A and a relatively thin metal by method B.

There is no limitation to a particular reconstruction technique, but may be any usual technique for generating tomographic images from projection data, as exemplified by the above Filtered Back Projection (FBP) method and an iterative approximation method (e.g. the Likelihood Expectation Maximization (ML-EM) method noted hereinbefore and the Shift Addition method noted hereinbefore). This step S1 corresponds to the extraction separation step in this invention.

(Step S2) Area Interpolation

Interpolation images are generated by interpolating the area of the metal or the like, from peripheral regions thereof, in the pre-interpolation projection data P2 extracted and separated in step S1. These interpolation images are regarded as post-interpolation projection data P3 as shown in FIG. 3. The post-interpolation projection data P3 corresponds to the interpolation images in this invention.

In this embodiment, labeling is first carried out for the pre-interpolation projection data P2 which is also binarized data. Although FIG. 4 depicts the area with "1" applied thereto (that is, the area of the metal or the like) as a square-shaped area indicated by a thick-line frame for expediency of description, the image area is of course not limited to the square-shaped area. As shown in FIG. 4(a), the image area S with "1" applied thereto, of the binarized data D (pre-interpolation projection data P2 in FIG. 3) is regarded as the square-shaped area indicated by the thick-line frame. Therefore, as shown in FIG. 4(b), "1" is applied inside the area S (see FIG. 4(a)), and "0" is applied outside the area S.

Next, in FIG. 4(b), in the image area S with "1" applied thereto (see FIG. 4(a)), those adjoining pixels "0" in directions outward of the area S are labeled "1", and those adjoining pixels "1" in directions outward of the area S are labeled "2" (see FIG. 4(c)). Further, in FIG. 4(c), in the image area S with "1" applied thereto, those adjoining pixels "0" in directions outward of the area S are labeled "1", those adjoining pixels "1" in directions outward of the area S are labeled "2", and those adjoining pixels "2" in directions outward of the area S are labeled "3" (see FIG. 4(d)). With labeling subsequently carried out in the same procedure, the labels will become higher toward the center of the area S and lower toward outside of the area S. Note, however, that the labeling is not limited to the technique shown in FIG. 4.

Based on the data labeled in this way, interpolation is carried out from the peripheral regions (peripheral pixels) in the projection data P1, using interpolation formulae like the following equations (1):

[Math 1]

$$I_n = \frac{1}{k} \sum_{m=1} p_m \cdot I_m \qquad (1)$$
$$p_m = 1 \text{ if } L_m < L_n$$
$$p_m = 0 \text{ if } L_m \geq L_n$$

In the above equations (1), n denotes pixels which are targets of interpolation, $I_n$ is a pixel value after interpolation of an n-th target pixel, k is the number of peripheral pixels less than the label of the n-th target pixel (that is, having labels lower in number than the label of the n-th pixel), m is a value when the peripheral pixels are put in the order m=1, 2, 3, ..., $p_m$ is a weighting factor of an m-th peripheral pixel, and $I_m$ is a pixel value (pixel value in the projection data P1) of the m-th peripheral pixel. However, when the label of the m-th peripheral pixel is set to $L_m$ and the label of the target pixel is set to $L_n$, $p_m$ is set to $p_m=1$ at the time of $L_m<L_n$ (that is, when the label of the m-th peripheral pixel is smaller than the label of the n-th pixel), and $p_m$ is set to $p_m=0$ at the time of $L_m \geq L_n$ (that is, when the label of the m-th peripheral pixel is larger than or equal to the label of the n-th pixel). Therefore, equations (1) above become equations for an additive average (arithmetic average) in which a sum total of pixel values of the peripheral pixels only at the time of $L_m<L_n$ (that is, the pixels closer to the living body tissue than the area of the metal or the like serving as the targets) is divided by the number k of peripheral pixels applicable to $L_m<L_n$. The number and range of peripheral pixels are determined arbitrarily.

The technique of interpolation is not limited to the above equations (1) using the labeling, but may be any usual technique of area interpolation, such as interpolation using pixel values of adjoining pixels as they are, or interpolation by conducting weighted additive averaging according to distances between pixels to be interpolated and peripheral pixels. This step S2 corresponds to the area interpolation in this invention.

(Step S3) First Tomographic Image Generation

Tomographic images are generated by reconstruction from the post-interpolation projection data P3 generated with the area of the metal or the like interpolated in step S2. These tomographic images are regarded as first tomographic images P4 as shown in FIG. 3. As noted also in step S2, there is no limitation to a particular reconstruction technique, but may be any usual technique for generating tomographic images from projection data, as exemplified by the FBP method and iterative approximation method. The first tomographic images P4 correspond to the tomographic images (generated in the first tomographic image generating step) in this invention. This step S3 corresponds to the first tomographic image generating step in this invention.

Although steps S4 and S5 are executed after step S3 in the flow chart in FIG. 2, steps S4 and S5 can be executed also before step S3. Therefore, instead of being limited to the flow chart in FIG. 2, step S3 may be executed after steps S4 and S5, or step S3 and steps S4 and S5 may be executed in parallel at the same time.

(Step S4) Metal or the Like Projection Data Generation

On the other hand, from differences between the projection data P1 acquired from the detection by the FPD 3 and the post-interpolation projection data P3 interpolated and generated in step S2, metal or the like projection data P5 which is projection data of the metal or the like is generated as shown in FIG. 3. This metal or the like projection data P5 corresponds to the extraneous projection data in this invention. This step S4 corresponds to the extraneous projection data generating step in this invention.

(Step S5) Second Tomographic Image Generation

Tomographic images are generated by reconstruction from the metal or the like projection data P5 generated in step S4. These tomographic images are regarded as second tomographic images P6 as shown in FIG. 3. The second tomographic images P6 correspond to the tomographic images (generated in the second tomographic image generating step) in this invention. As noted also in steps S2 and S3, there is no limitation to a particular reconstruction technique, but may be any usual technique for generating tomographic images from projection data, as exemplified by the FBP and iterative approximation method.

However, when the first tomographic images P4 are generated by the FBP method in step S3, the second tomographic images P6 are generated only by the FBP method in step S5. If synthesis were carried out by simply adding the tomographic images P4 and P6 together in step S6 to be described hereinafter, the results would be the original tomographic images from which artifacts are not removed, since the metal or the like projection data P5 used as the basis for the second tomographic images P6 is the difference between the projection data P1 and the post-interpolation projection data P3 used as the basis for the first tomographic images P4. Therefore, when the first tomographic images P4 are generated by the FBP method in step S3, the second tomographic images P6 are generated by the FBP method and replacement with a reference value in step S5.

The case of generating the second tomographic images P6 by the FBP method and replacement with a reference value will be described. When tomographic images are generated from the metal or the like projection data P5 by the FBP method, pixel values of the tomographic images may have negative values. So, tomographic images are generated by replacing with a set reference value the pixel values of areas lower than the reference value among the pixel values of the tomographic images generated by the FBP method, and the tomographic images with the replacement reference value are made the second tomographic images P6. Regarding the reference value, the pixel value as the reference value may usually be set to "0" only if the pixel values replaced with the reference value do not become negative values. Of course, the pixel value as the reference value may be set to a positive value.

When the first tomographic images P4 are generated by the FBP method in step S3, tomographic images with reduced artifacts are obtained even though the second tomographic images P6 are generated by the iterative approximation method in step S5 and synthesis is carried out by simply adding the tomographic imaged P4 and P6 together in step S6 to be described hereinafter. Therefore, the first tomographic images P4 may be generated by the FBP method in step S3, and the second tomographic images P6 by the iterative approximation method in step S5. When the FBP method is used in step S5, even though the iterative approximation method is used in step S3, the above replacement with the reference value is carried out for the second tomographic images P6. This step S5 corresponds to the second tomographic image generating step in this invention.

(Step S6) Tomographic Image Synthesis

The first tomographic images P4 generated in step S3 and the second tomographic images P6 generated in step S5 are synthesized. The tomographic images P4 and P6 may simply be added and synthesized together by simply adding both pixel values of the same pixels in the first/second tomographic images P4 and P6. The synthesis may be carried out by adding the first tomographic images P4 to the second tomographic images P6 resulting from the threshold process. Further, the synthesis may be carried out by adding the tomographic images P4 and P6 after multiplying each pixel value thereof by a coefficient as necessary. The synthesized tomographic images are regarded as synthetic tomographic images P7 as shown in FIG. 3. The synthetic tomographic images P7 correspond to the tomographic images (synthesized at the tomographic image synthesizing step) in this invention. This step S6 corresponds to the tomographic image synthesizing step in this invention.

According the radiation tomographic image generating method in this embodiment, the extraction separation in step S1 extracts and separates, from acquired radiological images (projection data P1 of X-ray images in this embodiment), images (pre-interpolation projection data P2 in this embodiment) of a substance (high-density substance such as metal in this embodiment) extraneous to a substance forming an area of interest in an inspection object (a substance forming the living body in this embodiment). The area interpolation in step S2 generates interpolation images (post-interpolation projection data P3 in this embodiment) by interpolating an area of the extraneous substance (area of the metal or the like in this embodiment), from peripheral regions thereof, in the images of the extraneous substance (pre-interpolation projection data P2) extracted and separated by the extraction separation in step S1. Then, the first tomographic image generation in step S3 generates tomographic images (first tomographic images P4 in this embodiment) from the interpolation images (post-interpolation projection data P3) generated with the area of the extraneous substance (area of the metal or the like) interpolated by the area interpolation in step S2. Since the area of the extraneous substance (area of the metal or the like) in the images of the extraneous substance (pre-interpolation projection data P2) extracted and separated by the extraction separation in step S1 is interpolated by the area interpolation in step S2, artifacts due to the extraneous substance (metal in this embodiment) are suppressed if tomographic images (first tomographic images P4) are generated by the first tomographic image generation in step S3 from the interpolation images interpolated and generated (post-interpolation projection data P3 in this embodiment). This enables observation of the area of interest (living body tissue in this embodiment) adjacent the area of the extraneous substance (adjacent the area of the metal or the like). As a result, the artifacts can be reduced while maintaining high spatial resolution.

In the radiation tomographic image generating method in this embodiment, it is preferable to comprise the metal or the like projection data generation in step S4 for generating extraneous projection data (metal or the like projection data P5 in this embodiment) which is projection data of the extraneous substance, from differences between the acquired radiological images (projection data P1 of the X-ray images) and the interpolation images (post-interpolation projection data P3 in this embodiment), the second tomographic image generation in step S5 for generating tomographic images (second tomographic images P6 in this embodiment) from the extraneous projection data (metal or the like projection data P5) generated by the metal or the like projection data generation in step S4, and the tomographic image synthesis in step S6 for synthesizing the tomographic images (first tomographic images P4) generated by the first tomographic image generation in the above step S3 and the tomographic images (second tomographic images P6) generated by the second tomographic image generation in step S5. Since the radiological images (projection data P1 of the X-ray images) are data including the extraneous portion (metal or the like) and the interpolation images (post-interpolation projection data P3) are data with the area of the extraneous substance (area of the metal or the like) interpolated, the projection data generated from the differences between the radiological images (projection data P1 of the X-ray images) and the interpolation images (post-interpolation projection data P3) becomes projection data of only the area of the extraneous substance (area of the metal or the like) (that is, extraneous projection data: metal or the like projection data P5 in this embodiment). Therefore, when the tomographic images (second tomographic images P6) are generated from the extraneous projection data (metal or the like projection data P5) by the second tomographic image generation in step S5, the generated tomographic images (second tomographic images P6) become tomographic images of only the area of the extraneous substance (area of the metal or the like). As a result, when the tomographic image synthesis in step S6 synthesizes both the tomographic images (first/second tomographic images P4 and P6) generated by the first/second tomographic image generations in steps S3 and S5, boundaries between the area of the extraneous substance (area of the metal or the like) and the other area (living body tissue in this embodiment) become clear in the area of interest while reducing the artifacts.

When the second tomographic image generation in step S5 generates tomographic images (second tomographic images P6) from the extraneous projection data (metal or the like projection data P5) by the FBP method, pixel values of the tomographic images (second tomographic images P6) may become negative values. So, the second tomographic image generation in step S5 generates tomographic images as second tomographic images P6 by replacing with a set reference value (e.g. pixel value "0" or a positive value) the pixel values of areas lower than the reference value among the pixel values of the tomographic images generated by the FBP method. Then, the tomographic image synthesis in step S6 synthesizes the tomographic images (first tomographic images P4) generated by the first tomographic image generation in step S3 and the tomographic images replaced with the reference value (second tomographic images P6) by the second tomographic image generation in step S5. As a result, even though the second tomographic image generation in step S5 generates the tomographic images (second tomographic images P6) from the extraneous projection data (metal or the like projection data P5) by the FBP method, natural tomographic images (synthetic tomographic images P7 in this embodiment) can be generated, with the pixel values of the tomographic images (second tomographic images P6) not becoming negative values, and the boundaries between the area of the extraneous substance (area of the metal or the like) and the other area (living body tissue) becoming clear in the area of interest.

As noted with reference to the flow chart of FIG. 2 also, the second tomographic image generation in step S5 may generate the tomographic images (second tomographic images P6) by the iterative approximation method. In this case, it may be combined with the FBP method in the first tomographic image generation in step S3. That is, the first tomographic image generation in step S3 generates the tomographic images (first tomographic images P4) by the FBP method, and the tomographic image synthesis in step S6 synthesizes the tomographic images (first tomographic images P4) generated by the FBP method in the first tomographic image generation in step S3 and the tomographic images (second tomographic images P6) generated by the iterative approximation method in the second tomographic image generation in step S5.

Similarly, the first tomographic image generation in step S3 may generate the tomographic images (first tomographic images P4) by the FBP method, or may generate the tomographic images (first tomographic images P4) by the iterative approximation method.

The extraction separation in step S1 noted hereinbefore may extract and separate the projection data (pre-interpolation projection data P2) of the images of the extraneous substance from the projection data (projection data P1) of the acquired radiological images (X-ray images), or may generate tomographic images from the projection data (projection data P1) of the acquired radiological images (X-ray images), extract and separate, from the tomographic images, tomographic images (pre-interpolation tomographic images) of the images of the extraneous substance, and forward project the extracted tomographic images (pre-interpolation tomographic images) of the images of the extraneous substance to generate projection data, thereby to extract and separate the projection data generated through the forward projection as the projection data (pre-interpolation projection data P2) of the images of the extraneous substance.

The radiation tomographic image generating program in this embodiment is a radiation tomographic image generating program for causing a computer (the CPU of the image processor 9 in FIG. 1) to perform radiation tomographic image generation for generating tomographic images based on a plurality of radiological images (X-ray images) acquired by radiation beams (X-ray beams in this embodiment) emitted from different directions to the inspection object M, respectively, which causes the computer (the CPU of the image processor 9) to perform the processes in steps S1-S6 in FIG. 2.

This invention is not limited to the foregoing embodiment, but may be modified as follows:

(1) The foregoing embodiment has been described taking X-rays as an example of radiation, but it may be applied to radiation (e.g. gamma rays) other than X-rays. Therefore, application can be made to a nuclear medicine diagnostic apparatus for acquiring transmission data by emitting radiation of the same type as a radioactive drug from an external radiation source to an inspection object.

Figure 7:
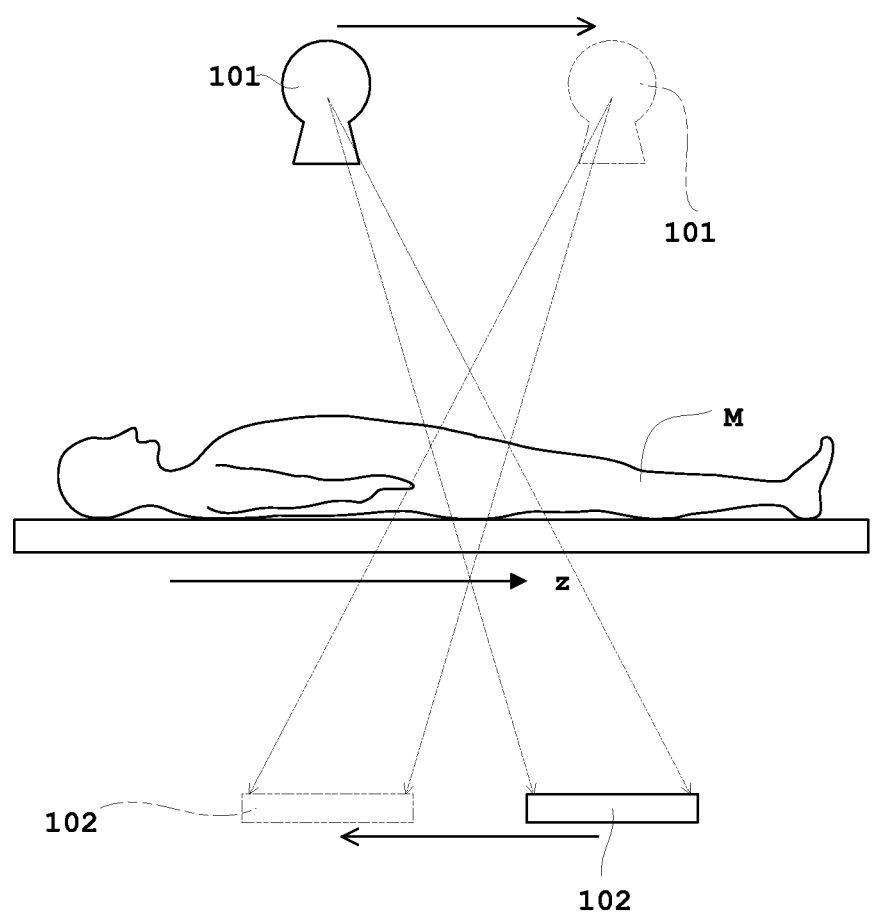
FIG. 7 is a side view showing an outline construction of a conventional tomographic apparatus for linear scanning.
Figure 8:
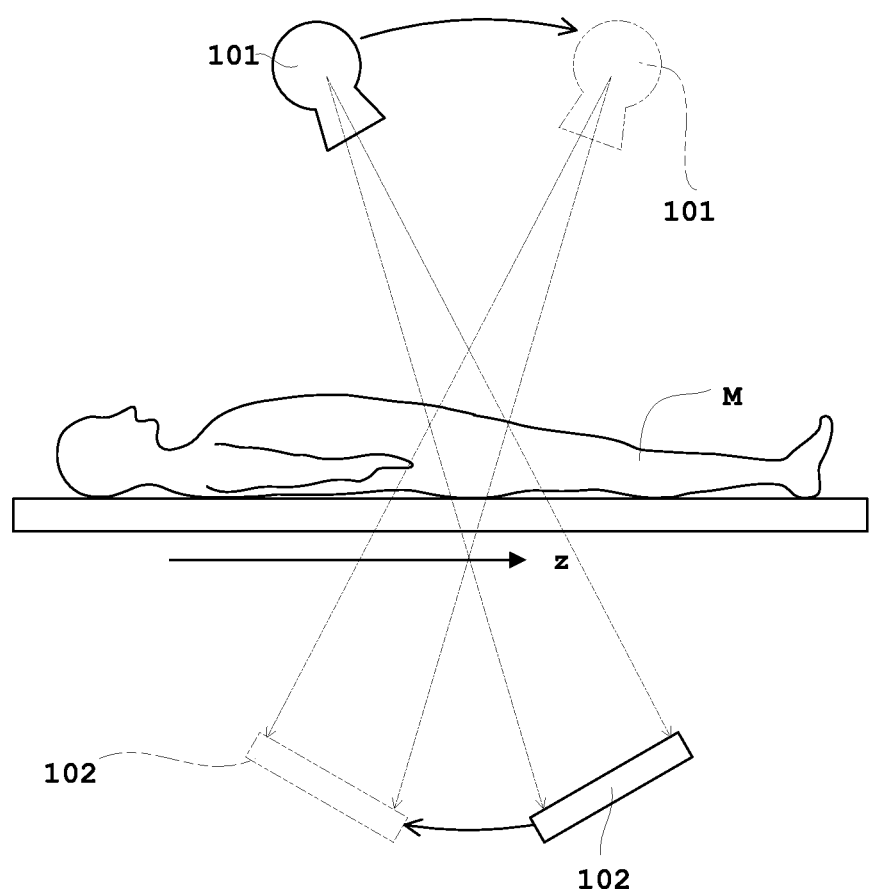
FIG. 8 is a side view showing an outline construction of a conventional tomographic apparatus for circular scanning.

(2) In the foregoing embodiment, a tomographic apparatus of the linear scan type as shown in FIGS. 1 and 7 is used, but application may be made to a tomographic apparatus with circular operation as shown in FIG. 8.

(3) The foregoing embodiment has been described taking a human body as an example of inspection object, has been described taking the substance forming a living body as an example of substance forming an area of interest in the inspection object, and has been described taking a high-density substance such as a metallic artificial joint, external fixator or dental stuffing as an example of extraneous portion. However, application may be made to radiographing of a low-density substance also. When the inspection object is other than the human body (e. g. when an object under inspection as used in a nondestructive testing apparatus is the inspection object), application can be made, whether high density or low density, to the case of extracting images of a substance extraneous to a substance forming an area of interest in the inspection object.

Figure 5:
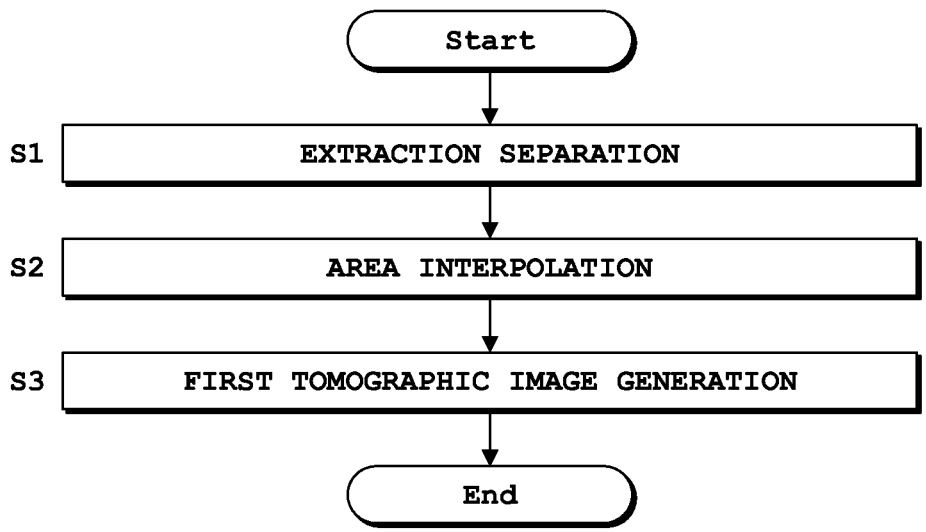
FIG. 5 is a flow chart showing a flow of a series of radiation tomographic image generation by the image processor according to a modification.
Figure 6:
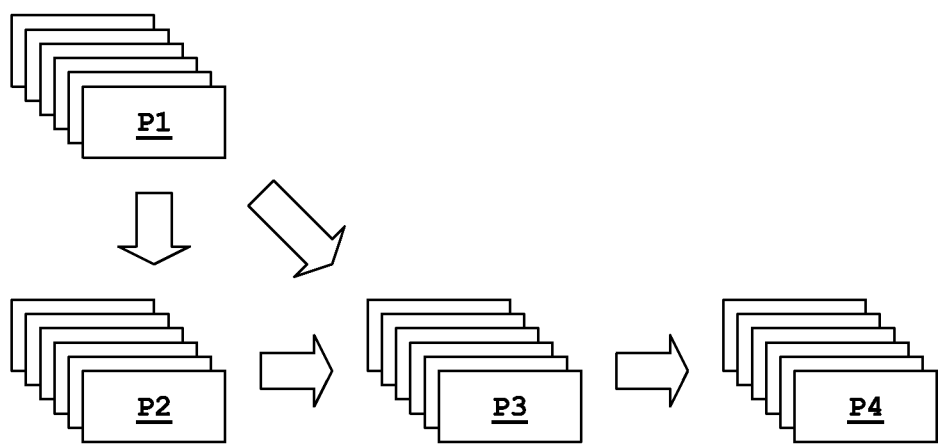
FIG. 6 is a schematic view showing a flow of each image and each data according to the modification.

(4) In the foregoing embodiment, and in the flow chart of FIG. 2, steps S4-S6, i.e. step S4 (metal or the like projection data generation), step S5 (second tomographic image generation) and step S6 (tomographic image synthesis), are executed. In FIG. 3, the metal or the like projection data P5 and the second tomographic images P6 are generated, and the first/second tomographic images P4 and P6 are synthesized to generate the synthetic tomographic images P7. However, it is not essential to execute steps S4-S6 unless it is necessary to check the boundaries between the area of the extraneous substance and the other area (living body tissue in the embodiment) in the area of interest. As shown in the flow chart of FIG. 5, step S1 (extraction separation), step S2 (area interpolation) and step S3 (first tomographic image generation) may be executed as a minimum requirement, and as in FIG. 6, only the pre-interpolation projection data P2, post-interpolation projection data P3 and first tomographic images P4 may be generated. The steps S1-S3 in FIG. 5 and the images and data in FIG. 6 are the same as the steps S1-S3 in FIG. 2 and the images and data in FIG. 3 of the foregoing embodiment, and therefore their description is omitted.

REFERENCE SIGNS LIST

9 . . . image processor
P1 . . . projection data
P2 . . . pre-interpolation projection data
P3 . . . post-interpolation projection data
P4 . . . first tomographic images
P5 . . . metal and the like projection data
P6 . . . second tomographic images
P7 . . . synthetic tomographic image

The invention claimed is:

1. A radiation tomographic image generating method for generating tomographic images based on a plurality of radiological images acquired by radiation beams emitted from different directions to an inspection object, respectively, the radiation tomographic image generating method comprising:
   an extraction separation step for extracting and separating, from the acquired radiological images, images of a substance extraneous to a substance forming an area of interest in the inspection object;
   an area interpolation step for generating interpolation images by interpolating an area of the extraneous substance, from peripheral regions thereof, in the images of the extraneous substance extracted and separated in the extraction separation step;
   a first tomographic image generating step for generating tomographic images from the interpolation images generated with the area of the extraneous substance interpolated in the area interpolation step;
   an extraneous projection data generating step for generating extraneous projection data which is projection data of the extraneous substance, from differences between the acquired radiological images and the interpolation images;
   a second tomographic image generating step for generating tomographic images from the extraneous projection data generated in the extraneous projection data generating step; and
   a tomographic image synthesizing step for synthesizing the tomographic images generated in the first tomographic image generating step and the tomographic images generated in the second tomographic image generating step.

2. The radiation tomographic image generating method according to claim 1, wherein:
   the second tomographic image generating step generates the tomographic images by replacing, with a set reference value, pixel values of areas lower than the reference value among pixel values of the tomographic images generated by a filtered back projection method; and
   the tomographic image synthesizing step synthesizes the tomographic images generated in the first tomographic image generating step and the tomographic images replaced with the reference value in the second tomographic image generating step.

3. The radiation tomographic image generating method according to claim 1, wherein the second tomographic image generating step generates the tomographic images by an iterative approximation method.

4. The radiation tomographic image generating method according to claim 3, wherein:
   the first tomographic image generating step generates the tomographic images by a filtered back projection method; and
   the tomographic image synthesizing step synthesizes the tomographic images generated by the filtered back projection method in the first tomographic image generating step and the tomographic images generated by the iterative approximation method in the second tomographic image generating step.

5. The radiation tomographic image generating method according to claim 1, wherein the first tomographic image generating step generates the tomographic images by a filtered back projection method.

6. The radiation tomographic image generating method according to claim 1, wherein the first tomographic image generating step generates the tomographic images by an iterative approximation method.

7. The radiation tomographic image generating method according to claim 1, wherein the extraction separation step extracts and separates projection data of the images of the extraneous substance from projection data of the acquired radiological images.

8. The radiation tomographic image generating method according to claim 1, wherein the extraction separation step generates tomographic images from projection data of the acquired radiological images, extracts and separates, from the tomographic images, tomographic images of the images of the extraneous substance, and forward projects the extracted tomographic images of the images of the extraneous substance to generate projection data, thereby to extract and separate the projection data generated through the forward projection as the projection data of the images of the extraneous substance.

9. A non-transitory computer-readable medium storing a radiation tomographic image generating program for causing a computer to perform radiation tomographic image generation for generating tomographic images based on a plurality of radiological images acquired by radiation beams emitted from different directions to an inspection object, respectively, the radiation tomographic image generating program comprising:

an extraction separation step for extracting and separating, from the acquired radiological images, images of a substance extraneous to a substance forming an area of interest in the inspection object;

an area interpolation step for generating interpolation images by interpolating an area of the extraneous substance, from peripheral regions thereof, in the images of the extraneous substance extracted and separated in the extraction separation step;

a first tomographic image generating step for generating tomographic images from the interpolation images generated with the area of the extraneous substance interpolated in the area interpolation step;

an extraneous projection data generating step for generating extraneous projection data which is projection data of the extraneous substance, from differences between the acquired radiological images and the interpolation images;

a second tomographic image generating step for generating tomographic images from the extraneous projection data generated in the extraneous projection data generating step; and a tomographic image synthesizing step for synthesizing the tomographic images generated in the first tomographic image generating step and the tomographic images generated in the second tomographic image generating step, the computer being caused to perform the processes in these steps.

* * * * *